US010149878B2

(12) United States Patent
Bhaskaran et al.

(10) Patent No.: US 10,149,878 B2
(45) Date of Patent: Dec. 11, 2018

(54) USE OF FENUGREEK EXTRACT TO ENHANCE FEMALE LIBIDO

(71) Applicant: GE NUTRIENTS, INC., Anaheim, CA (US)

(72) Inventors: Sunil Bhaskaran, Pune (IN); Ramasamy V. Venkatesh, Haikou (CN); Jith Veeravalli, Anaheim, CA (US)

(73) Assignee: GE Nutrients, Inc., Anaheim, CA (US)

( * ) Notice: Subject to any disclaimer, the term of this patent is extended or adjusted under 35 U.S.C. 154(b) by 0 days.

(21) Appl. No.: 14/097,465

(22) Filed: Dec. 5, 2013

(65) Prior Publication Data

US 2014/0154346 A1    Jun. 5, 2014

Related U.S. Application Data

(60) Provisional application No. 61/733,668, filed on Dec. 5, 2012.

(51) Int. Cl.
*A61K 36/48* (2006.01)
(52) U.S. Cl.
CPC .................................. *A61K 36/48* (2013.01)
(58) Field of Classification Search
CPC ..... A61K 2300/00; A61K 36/74; A61K 36/48
See application file for complete search history.

(56) References Cited

U.S. PATENT DOCUMENTS

| | | | |
|---|---|---|---|
| 5,731,339 A | 3/1998 | Lowrey | |
| 6,060,063 A | 5/2000 | Lansky | |
| 2003/0175329 A1 | 9/2003 | Azarnoff et al. | |
| 2005/0153001 A1* | 7/2005 | Aburdeineh et al. | 424/757 |
| 2008/0299235 A1 | 12/2008 | Aburdeineh et al. | |
| 2010/0303937 A1* | 12/2010 | Farber | 424/757 |

FOREIGN PATENT DOCUMENTS

| | | |
|---|---|---|
| JP | 2003505345 A | 2/2003 |
| JP | 2004-67590 A | 3/2004 |
| JP | 2004536822 A | 12/2004 |
| JP | 2005112832 A | 4/2005 |
| JP | 2012140437 A | 7/2012 |
| RU | 2239424 C2 | 11/2004 |

OTHER PUBLICATIONS

Website document entitled: "Fenugreek is a Mom's Best Friend" (available at http://thestircafemom.com/baby/121966/fenugreek_is_a_moms_best). Dated Jun. 20, 2011. Downloaded from website Nov. 20, 2014.*
Website document entitled: "Increase Your Libido for Women" (available at http://www.eboards4all.com/735587/messages/2538.html). Dated Sep. 6, 2008. Downloaded from website Nov. 20, 2014.*
Website document entitled "SexMedications" (available at http://www.sex-medications.sexinformations.com/increasing-your-sexual-desire-and-drive-4.html). Archived to May 25, 2012. Dowloaded from website Nov. 20, 2014.*
Steels et al. (2011) Phytother. Res. 25: 1294-1300.*
Ahirwar et al. (2010) Der Pharmacia Sinica, 1 (3): 33-39.*
Anonymous: "Tremendous Natural Remedies For Low Female Libido—How to Use Home Remedies to Increase Female Libido | lady Care Health", Sep. 3, 2012 (Sep. 3, 2012), XP055277594, Retrieved from the Internet: URL:http://web.archive.org/web/20120903110158/ttp://www.ladycarehealth.com/tremendous-natural-remedies-for-low-female-libido [retrieved on Mar. 6, 2016].
Rao Amanda et al: "Influence of a Specialized Trigonella foenum-graecum Seed Extract (Libifem), on Testosterone, Estradiol and Sexual Function in Healthy Menstruating Women, a Randomised Placebo Controlled study", Phytotherapy Research, vol. 29, No. 8, Aug. 2015 (Aug. 2015), pp. 1123-1130, XP009190310, ISSN: 0951-418X.
Anonymous: "Libifem(TM)-Gencor", Jul. 28, 2013 (Jul. 28, 2013), XP055277586, Retrieved from the Internet: URL:http://web.archive.org/web/20130728090045/http://gencorpacific.com/index.php/featured-ingredients/libifem [retrieved on Jun. 3, 2016].
Extended European Search Report in Application No. 13860280.0-1466, dated Jun. 21, 2016.
Mohammad Azam Khan; Muheet-e-Azam vol. II ( Part I) (19th century AD), Matba Nizami, Kanpur, 1985 AD p. 147.
Mohammad Shareef Khan; Ilaaj-al-Amraaz (18th century AD), Afzal-al- Matabe, Barqi Press, Delhi, 1921 AD p. 282.
Ziya Al-Din Abdullah Ibn Al-Baitar; Al-Jaam'e-li-Mufradaat-al-Advia-wal-Aghzia, vol. II (13th century AD), Matba Amra, Cairo, Egypt, 1874 AD p. 25.
Abu Bakr Mohammad.Bin Zakariyya Al-Razi; Kitaab-al-Haawi-fil-Tibb, vol. XX (9th century AD), Dayerah-al- Ma'aarif Usmania, Hyderabad, (First Edition) 1967 AD p. 309.
Third Party Observation under Section 27 in Australian Patent Application No. 2013355181, dated Nov. 30, 2015.
"Natural treatment for dry vagina—Treat vaginal dryness—Dry vagina cures | Free Consultation by AyurvedicCure.com," Oct. 18, 2012, XP055359844.
Arcos, "Female Sexual Function and Response," JAOA, Supplement 1, vol. 104, No. 1, pp. S16-S20 (2004).
Battaglia C et al., "Menstrual cycle-related morphometric and vascular modifications of the clitoris," J. Sex. Med. 5(12):2853-2861 (2008).
Bullivant SB, et al., "Women's sexual experience during the menstrual cycle: Identification of the sexual phase by noninvasive measurement of luteinizing hormone," J. Sex. Res. 41(1):82-93 (2004) (Abstract).
Cohen et al., "A Global Measure of Perceived Stress," J. Health and Social Behavior, vol. 24, No. 4, pp. 385-396 (Dec. 1983).

(Continued)

*Primary Examiner* — Christopher R Tate
*Assistant Examiner* — Russell G Fiebig
(74) *Attorney, Agent, or Firm* — Venable LLP; Keith G. Haddaway; Kerri M. Patterson (57) ABSTRACT

The invention is a method of enhancing female libido by administering an effective amount of a fenugreek extract, for example fenugreek seed extract, to a female in need of enhanced libido. The female can be a human female.

16 Claims, 6 Drawing Sheets

(56) References Cited

OTHER PUBLICATIONS

Guillermo et al., "Female social and sexual interest across the menstrual cycle: the role of pain, sleep and hormones," BMC Women's Health, 10:19, pp. 1-10 (2010).
Haselton et al., "Conditional expression of women's desires and men's mate guarding across the ovulatory cycle,"Horm. Behay. 49(4):509-518 (2006).
Jones BC et al., "Commitment to relationships and preferences for femininity and apparent health in faces are strongest on days of the menstrual cycle when progesterone level is high," Horm. Behay. 48(3):283-290 (2005) (Abstract).
Meston, "Validation of the Female Sexual Function Index (FSFI) in women with female orgasmic disorder and in women with hypoactive sexual desire disorder," J. Sex Marital Ther., 29(1):39-46 (2003) (Abstract).
Pillsworth EG, et al., "Ovulatory shifts in female sexual desire," J. Sex. Res. 41(1):55-65.
Rosen et al., "The Female Sexual Function Index (FSFI): A Multidimensional Self-Report Instrument for the Assessment of Female Sexual Function," Journal of Sex & Marital Therapy, 26:191-208 (2000).
Salonia et al., "Menstrual cycle-related changes in circulating androgens in healthy women with self-reported normal sexual function," J. Sex Med. 5(4):854-863 (2008).
Spanier, "Measuring Dyadic Adjustment: New Scales for Assessing the Quality of Marriage and Similar DYads," Journal of Marrage and the Family, vol. 38, No. 1, pp. 15-28 (Feb. 1976).
Stage S, "Female Complaints—Lydia Pinkham the Business of Women's Medicine," WW. Norton & Co., New York, p. 304, 1999 (Abstract).
Steels et al., "Physiological Aspects of Male Libido Enhanced by Standardized Trigonella foenum-graecum Extract and Mineral Formulation," Phytotherapy Res. Published online in Wiley Online Library DOI: 10.1002/ptr.3360, 7 pages (2011).
Stein et al, "A Multidimensional Measure of Fatigue for Use with Cancer Patients," Cancer Practice, 6, 143-152 (1998) (Abstract).
Stein et al., "Further Validation of the Multidimensional Fatigue Symptom Inventory-Short Form," J. Pain Symptom Manage., 27(1):14-23 (Jan. 2004).
Turna et al., "Women with low libido: correlation of decreased androgen levels with female sexual function index," Int. J. Impot. Res. 17(2):148-53 (2005).

Weigel et al, "The female sexual function index (FSFI): cross-validation and development of clinical cutoff scores," J Sex Marital Ther., 31(1):1-20 (2005) (Abstract).
Wilcox et al., "On the frequency of intercourse around ovulation: Evidence for biological influences," Human Reproduction 19(7):1539-1543 (2004).
Office Action issued in Japanese Patent Application No. 2012-545851, dated Sep. 5, 2017.
Office Action received in Japanese Application No. 2015-545851 dated Jul. 3, 2018.
Aradhana et al. "Diosgenin—A growth stimulator of mammary gland of ovariectomized mouse," Indian Journal of Experimental Biology 30(5):367-7 (1992).
Blumenthal M et al., "Herbal Medicine: Expanded Commission E Monographs," Integrative Medicine Communications pp. 130-133 (2000).
Davis, et al. "Oral contraceptives and libido in women," Ann. Rev. Sex. Res. 15:297-320 (2004).
Davis S., et al. "Circulating androgen levels and self-reported sexual function in women," JAMA, vol. 294, No. 1, pp. 1-96 (2005).
Davis S., et al. "Testosterone for low libido in postmenopausal women not taking estrogen," N. Engl. J. Med. 359:2005-2017 (2008).
Gangestad et al., "Human oestrus," Proceedings of the Royal Society B: Biological Sciences 275(1638): 991-100 (2008).
Gueguen, "The receptivity of women to courtship solicitation across the menstrual cycle: A field experiment," Biol. Psychol. 80(3):321-324 (2009).
Jones et al. "Effects of menstrual cycle phase on face preferences," Archives of Sexual Behavior. 37:78-84 (2008).
Nyunt A, et al., "Androgen status in healthy premenopausal women with loss of libido," J. Sex. Marital Ther. 31 (1):73-80 (2005).
Website Article. "12 best natural home remedies for increasing femal libido," Best Health Tips, Sep. 2012. (available at https://web.archive.org/web/20121015121648/http:/www.bhtips.com/2012/09/12-best-natural-home-remedies-for.html).
Kalinchenko et al., "Modern pharmacology of female sexual dysfunctions," Magazine, The Attending Physician (2009), retrieved from <https:/www.lvrach.ru/2009/08/10520337> on Dec. 15, 2017, 16 pages.
Basson et al., "Pharmacotherapy for women's sexual dysfunction," Expert Opin. Pharmacother., 10(10): pp. 1631-1648, 2009 (Abstract only).

* cited by examiner

USE OF FENUGREEK EXTRACT TO ENHANCE FEMALE LIBIDO

CROSS-REFERENCE TO PRIOR APPLICATIONS

U.S. Provisional Application No. 61/733,668, filed on Dec. 5, 2012.

BACKGROUND OF THE INVENTION

Area of the Art

The present invention relates to methods of enhancing female sexual drive and libido. In particular, the invention is a method of enhancing female libido by administering a fenugreek extract.

Description of the Background Art

The Global Study of Sexual Attitude and Behaviours conducted in 27,500 men and women in 30 countries indicates that lack of interest in sex was reported by 18% men and lack of pleasure from sex was reported by 11% of the participating men. (Basch et al, 1993). Although female sexual dysfunction is a problem with low priority, it can have a profound impact on quality of life. In women, the cycle of sexual response begins in the brain, where a memory, an image, a scent, music, or a fantasy acts as a trigger to prompt sexual arousal. Decreased libido, altered arousal, inability to achieve orgasm, and dyspareunia are the four broad types of sexual dysfunction in women. Decreased libido results in delayed or altered arousal, decreased vaginal lubrication and dilation, delayed or absent orgasm, and pain or dyspareunia, which can lead to an aversion to sexual experiences. (Arcos, B Female sexual function and response. J. Am. Osteopath. Assoc. 104:S16-20 (2004).)

There has been significant interest in nutritional therapies for sexual function and performance. Some of these therapies have stood the test of time, afforded by their traditional use, while some of these have undergone scientific scrutiny to investigate their evidence for efficacy. However, most of these nutritional supplements have not been tested in rigorous clinical trials. Many trials investigating these supplements have had serious design flaws such as lack of placebo group or effective blinding techniques.

SUMMARY OF THE INVENTION

In summary, the invention is a method of enhancing female libido by administering an effective amount of a fenugreek extract to a female in need of enhanced libido. The female can be a mammal. The female can also be a human female. The fenugreek extract can be fenugreek seed extract. The enhanced female libido can be measured as the modification of a behavioral characteristic indicative of an increase in female libido. For example, the modification of a behavioral characteristic can be one or more of increasing sexual fantasy, increasing arousal, increasing sex drive, enhancing partner relationship and increasing desire for sexual activity. The enhanced female libido can also or alternatively be measured as a modification of a biological response indicative of an increase in female libido. For example, the modification of a biological response can be one or more of increasing an ability to achieve orgasm, decreasing dyspareunia, and increasing vaginal lubrication or dilation. In other examples, the biological response is a change in the level of a sex steroid or hormone. For example, a change in the level of one or more of total testosterone, free testosterone, sex hormone binding globulin, total estradiol (or oestradiol), free estradiol (E2), androstenedione, dehydroepiandrosterone (DHEA), dehydroepiandrosterone sulfate (DHEAS), Follicle Stimulating Hormone (FSH), and Luteinizing Hormone (LH). Enhanced feale libido can also be measured using various scoring techniques known in the art. For example, enhanced female libido can be evidenced by a statistically significant increase in one or more DISF domain scores, or a statistically significant increase in one or more FSFI domain scores or in total FSFI score.

In some embodiments the fenugreek seed extract is administered in an amount of from about 300 to about 1000 mg per day. In some embodiments, the fenugreek seed extract is administered in an amount of about 600 mg per day. In exemplary embodiments, the total daily dose is administered as two approximately equal doses. The fenugreek seed extract can be administered approximately one hour before a meal, for example about one hour before a morning meal and one hour before an evening meal. In exemplary embodiments the fenugreek extract is administered orally, for example in the form of a capsule.

The present invention succeeds where previous efforts have failed by providing an herbal composition that enhances female libido. This invention solves a problem previously thought to be insoluble by providing a treatment that enhances female libido as measured by behavioral and/or biological factors. This invention satisfies a long felt need for safe and effective enhancement of female libido.

Further objectives and advantages, as well as the structure and function of preferred embodiments will become apparent from a consideration of the description, and non-limiting examples that follow.

DESCRIPTION OF THE FIGURES

FIG. 4 shows FSFI Arousal domain score and Total score at Basline and month 2 in the active treatment and placebo groups.

FIG. 6 shows the average free testosterone and sex hormone binding globulin levels at baseline and month 2 in the active treatment group and placebo groups.

DETAILED DESCRIPTION OF THE INVENTION

Embodiments of the invention are discussed in detail below. In describing embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

Female changes in sexual function and social-sexual behavior can be complex due to natural cyclical changes in hormonal activity. Thus, to assure effectiveness, it is often necessary to show observed effects over 2 menstrual cycles with assessment generally conducted at the beginning (day 1) of each cycle. Subtle shifts in female libido across the menstrual cycle and somewhat less noticeable changes in socio-sexual behavior have been previously noted (Bullivant S B, et al. Women's sexual experience during the menstrual cycle: Identification of the sexual phase by noninvasive measurement of luteinizing hormone J. Sex. Res. 41(1):82-93 (2004); Wilcox A J, et al. On the frequency of intercourse around ovulation: Evidence for biological influences. Human Reproduction 19(7):1539-1543 (2004).) Behavioral changes that support favorable mating strategies coincide with times of high fertility, ovulation, and higher estrogen concentrations (Pillsworth E G, et al Ovulatory shifts in female sexual desire. J. Sex. Res. 41(1):55-65, et al.) Thus, increase in libido can also be assessed behaviorally, for example by evaluation of daily diary entries regarding sexual interest and sexual encounters.

A number of projects have supported a functional role for cyclic socio-sexual behavioral changes (Gangestad S W, et al. Human oestrus. Proceedings of the Royal Society B: Biological Sciences 275(1638):991-100 (2008).) Some studies suggest such behavior may be linked to estrogen/progesterone ratios. Around the time of ovulation, normally cycling women commonly experience increased libido, sexual interest and attraction towards potential mates (Jones et al, 2008) Women report feeling more attractive, have more interest in attending events where they might meet men, experience more mate guarding by their partner (Haselton M G, et al. Conditional expression of women's desires and men's mate guarding across the ovulatory cycle. Horm. Behay. 49(4):509-518 (2006)) and are more likely to provide a phone number to a prospective mate during the late follicular/high estrogen phase (Gueguen The receptivity of women to courtship solicitation across the menstrual cycle: A field experiment. Biol. Psychol. 80(3):321-324 (2009)). Conversely, during the luteal phase or high progesterone phase, women report higher commitment to their relationships. They also tend to prefer more feminized male faces that has been postulated to represent a shift towards a desire for longer term social support (Jones B C, et al. Commitment to relationships and preferences for femininity and apparent health in faces are strongest on days of the menstrual cycle when progesterone level is high. Horm. Behay. 48(3):283-290 (2005).).

In one study, female sexual function has been shown to increase during the ovulatory phase of the menstrual cycle, in congruence with rising free and total testosterone (Salonia A, et al. Menstrual cycle-related changes in circulating androgens in healthy women with self-reported normal sexual function. J. Sex. Med. 5(4):854-863 (2008).) However, Battaglia et al. reported no significant variation in androgens across the cycle but mention that additional synthesis and metabolism at the adrenal glands and peripheral tissues make it difficult to accurately correlate a specific androgen to sexual function. (Battaglia C, et al. Menstrual cycle-related morphometric and vascular modifications of the clitoris. J. Sex. Med. 5(12):2853-2861 (2008).)

In a similar study, Guillermo et al, 2010 found associations between hormones and socio-sexual questions, with the exception of progesterone. At mid-cycle, higher cortisol was associated with "enjoying the company of the other" for the control group, whereas higher estradiol and dehydroepiandrosterone sulphate (DHEAS) concentrations were linked positively to task attraction in the oral contraceptive (OC) group. During the luteal phase, higher estradiol and estriol were associated with sexual interest questions in the control group, whereas higher progesterone was associated with more social attraction and better work interactions in the OC group. In addition, higher luteal DHEAS meant lower social and physical attraction for the OC group.

These findings are also supported by other studies that link low female libido and hypoactive sexual disorder with altered hormone levels. In 2005, Davies et al., demonstrated that long term treatment (12 months) of women with hypoactive sexual disorder with 300 μg/day testosterone was associated with an increased frequency of satisfying sexual encounters, increase in desire and decrease in stress.

Turna observed significant differences in the full-scale Female Sexual Function Index (FSFI) score for both pre- and postmenopausal women between women with low libido and controls in total testosterone, free testosterone and DHEAS levels. (Turna B, et al. Women with low libido: correlation of decreased androgen levels with female sexual function index Int. J Impot. Res. 2005 17(2):148-53) In addition, decreased total testosterone, free testosterone and DHEAS levels positively correlated with full-scale FSFI score and FSFI-desire, FSFI-arousal, FSFI-lubrication and FSFI-orgasm scores. This suggests that women with low libido have lower androgen levels compared to age-matched normal control groups and their decreased androgen levels correlate positively with female sexual function index domains.

In contrast, Nyunt et al. undertook a study of 29 premenopausal women with reduced libido (subjects) and 12 healthy females (controls) and looked for relationship between sexual drive and serum estradiol, total testosterone, and dihydrotestosterone (DHT), DHEAS, and sex steroid-binding globulin (SHBG) levels. (Nyunt A, et al. Androgen status in healthy premenopausal women with loss of libido. J. Sex. Marital Ther. 31(1):73-80 (2005).) Subjects were more likely than controls to have low income, a minor illnesses, a history of depression and to report sexual problems in their partners. Loss of libido in otherwise healthy women may also therefore be related to relationship problems, depression, psychosocial factors, and sexual dysfunction in the partner but do not appear to be related to androgen status.

Davis and Castano conducted a review of 30 published articles of the effects of OCs on sexual functioning and concluded that the results were inconclusive and better-designed studies are needed to establish the independent, causal effects of OCs on libido. (Davis A R, Castafto P M Oral contraceptives and libido in women. Ann. Rev. Sex. Res. 2004; 15:297-320.) Treatment with serotonin-specific reuptake inhibitors (SSRIs) and other antidepressants may cause decreased libido and orgasm problems. Antipsychotic treatment often causes libido, lubrication, and orgasm problems. Spironolactone may cause decreased libido and impaired lubrication.

The study and treatment of female libido problems is complex, can have multiple sources of causation and be manifest in a number of ways. Accordingly, there is a continuing need for treatments that enhance female libido. By identifying a successful treatment, hormonal aspects, physical aspects (stress and fatigue) and behavioral and relationship aspects that may affect or be affected by female libido can be better understood. The present invention relates to an herbal extract that is useful in enhancing female libido.

Fenugreek (*Trigonella foenum-graecum*) is an herb used in some traditional Indian cooking. In addition to its culinary uses, fenugreek seeds are believed by some to increase milk supply in lactating women. It is a well-studied herb with an excellent safety profile. It is on the Australian Register of Therapeutic Goods (ARTG) list of approved ingredients. Fenugreek extracts, particularly Fenugreek seed extracts, contain a variety of active compounds, including possibly more than a 100 phytochemical constituents. Among the important constituents are Furostanol Saponins and Steroidal Saponins. For example, Fenugreek contains Protodioscin, Pseudo Protodioscin, Gracillin, Protogracillin, Diosgenin, Dioscin and many other saponins and sapogenins. Diosgenin is an important precursor for the synthesis of a number of sex hormones, and has been shown to exhibit estrogenic effects. (Aradhana A, et al. Indian Journal of Experimental Biology 30(5):367-7 (1992).) Other saponins have not yet been identified with specificity. Fenugreek extracts may also include choline, trimethylamine (a sex hormone in frogs), Vitamins A, B2, B6, B12, D, and essential oils. (Blumenthal M, et al. Herbal Medicine: Expanded Commission E Monographs. Integrative Medicine Communications pp. 130-133 (2000).)

The saponins present in fenugreek extracts exist predominately as saponin glycosides. Fenugreek extracts can be standardized in one or more saponins in order to provide proper comparative analysis. Commercially available Fenugreek seed extracts can be used in accordance with the invention, although none have been previously proposed for enhancement of female libido. An exemplary standardized fenugreek seed extract is marketed under the name LIBIFEM® available from Gencor Pacific Inc. (Anaheim, Calif.)

Previous studies have shown that fenugreek seed extract has a positive effect on male libido, muscle growth and energy as well as obesity and diabetes. It has been theorized that the wide-ranging therapeutic actions of the herb may be mediated through hormone regulation, in particular the Insulin-like growth factor 1 (IGF-1) pathways. (Steels E, et al. Physiological Aspects of Male Libido Enhanced by Standardized *Trigonella foenum-graecum* Extract and Mineral Formulation. Phytotherapy Res. Published online in Wiley Online Library DOI: 10.1002/ptr.3360 (2011).) Although not previously observed, libido in women can also be enhanced by administering fenugreek, fenugreek extract and fenugreek seed extract. Enhanced libido can also result from behavioral changes or by modulation of the hormone axis.

In general, fenugreek seed extracts useful in the invention can be obtained by known methods used to extract fenugreek seeds. Methods include aqueous extraction, alcoholic extraction, extraction with polar organic solvents and extraction with non-polar organic solvents. Mixtures of solvents can also be used. For example, fenugreek and fenugreek seeds may be extracted with water, alcohols such as methanol or ethanol, or combinations thereof.

Increased libido in women can be manifest in a number of ways. The most common ways of assessing an increase in libido are based on either behavioral changes or biological responses. Administration of fenugreek seed extract as described elsewhere herein has a beneficial effect on female sexual function in general and on one or more individual parameters of female sexual function as measured by behavioral changes or biological responses.

Behavioral changes associated with increased libido in women can include, for example, one or more of increasing sexual fantasy, increasing arousal, increasing sex drive, enhancing partner relationship and increasing desire for sexual activity. Other behavioral changes might include frequency of sexual encounters, subjective quality of current sexual functioning, effects on stress and fatigue, sexual distress, relational intimacy and effects on general health parameters including energy. According to an embodiment of the present invention, administration of an effective amount of fenugreek seed extract enhances at least one behavioral change indicative of an increase in female libido.

Another commonly used and widely accepted assessment tool for behavioral changes is the Derogatis Interview for Sexual Functioning (Female) (DISF female) which can be administered by an interviewer or as a self-assessment in a self-reporting version (DISF-SR) that asks essentially the same questions. The DISF evaluates the quality of current sexual functioning in a multi-domain format, which parallels the phases of the sexual response cycle into five domains of sexual functioning: (1) Sexual Cognition/Fantasy, (2) Sexual Arousal, (3) Sexual Behavior/Experience, (4) Orgasm, and (5) Sexual Drive/Relationship. In addition, the DISF Total Score is computed, which summarizes the quality of sexual functioning across the five primary DISF domains. The DISF interview requires between 15 to 20 minutes to complete, and there are distinct gender-keyed versions for men and women. Scores are reported as DISF-SR QOL (Quality of Life) scores.

Fatigue can be assessed using the Multidimensional Fatigue Symptom Inventory (MFSI). (See, e.g., Stein, *J Pain Symptom Manage.* 2004 January; 27(1): 14-23; Stein et al, *Cancer Practice,* 6, 143-152 (1998).) MFSI provides a total score for fatigue and also included at individual domains of general, emotional, physical, mental and vigor as separate aspects of fatigue.

Stress can be evaluated on the Perceived Stress Scale (PSS). (See, e.g., Cohen et al. J. Health and Social Behavior, Vol. 24, No. 4 (December 1983), pp. 385-396.) PSS is the most widely used psychological instrument for measuring the perception of stress. It is a measure of the degree to which situations in one's life are appraised as stressful. Items were designed to tap how unpredictable, uncontrollable, and overloaded respondents find their lives. The scale also includes a number of direct queries about current levels of experienced stress.

Relationship quality can be evaluated using the Dyadic Adjustment Scale (DAS). (See, e.g., Spanier, *J. Marriage and the Family*, Vol. 38, No. 1 (February 1976), pp. 15-28.) The DAS is a 32-item measure of relationship quality with their partner. The and Dimensional Relationship Quality (DRQ) measure was used to assess the health of the relationship of the participant and their partner. It is a 32-item measure of relational intimacy. This DRQ subscale has been shown to be reliable and valid measures of relationship intimacy across multiple countries. The intimacy subscale includes items assessing empathy, openness, and trust in the relationship. Items consist of Likert responses coded so that higher scores indicate higher relational intimacy. Subscale scores are obtained by summing individual items.

A number of biological responses can be measured to evaluate enhancement of female libido. Biological responses can include, for example, increasing an ability to achieve orgasm, decreasing dyspareunia, and increasing vaginal lubrication or dilation. According to an embodiment of the present invention, administration of an effective amount of fenugreek seed extract results in a change to at least one biological response indicative of an increase in female libido. A biological response can also be measured by measuring a change in the level of a sex steroid or hormone. Examples of sex steroids or hormone levels that can be measured include, for example, total testosterone, free testosterone, sex hormone binding globulin total estradiol free estradiol (E2), anclrostenedione, Dehydroepiandrosterone (DHEA), Dehydroepiandrosterone sulfate (DHEAS), Follicle Stimulating Hormone (FSH), and Luteinizing Hormone (LH). According to an embodiment of the present invention, administration of an effective amount of fenugreek seed extract results in a change in the level of a sex steroid or hormone indicative of an increase in female libido.

Enhancement of female libido is achieved by administering an effective amount of fenugreek seed extract to a female in need of enhancement of libido. The female is usually a mammal and can be a human. The effective amount can be, for example, two daily doses of about 150 mg to about 500 mg (i.e., about 300 mg to about 1000 mg per day). In exemplary embodiments, the amount administered is two daily doses of about 250 mg to about 400 mg (i.e., about 500 mg to about 800 mg per day) or two daily doses of about 300 mg (i.e., about 600 mg per day). Because of the safety profile associated with fenugreek extract, higher daily doses are possible, for example up to about 1500 mg per day, up to about 2000 mg per day, up to about 2500 mg per day, or up to about 3000 mg per day. As will be appreciated, a variety of unit dosage forms can be administered, and the total daily intake can be divided into two, three, four or more doses spread out through the day to provide the desired or necessary total daily dose. In exemplary embodiments, the fenugreek seed extract is administered approximately one hour before meals, for example about one hour before a morning meal and about one hour before an evening meal.

To balance out hormonal changes associated with menstruation, fenugreek seed extract can be administered over a period of at least four weeks or at least eight weeks. In exemplary embodiments, the administration is continued indefinitely. Administration may be halted temporarily to assess whether continued administration is necessary. For example, administration can be halted for about four weeks or about eight weeks after which libido is again assessed. If libido remains high and does not fall to pre-administration levels, administration can be stopped. Testing should continue periodically to assure that no further decline in libido is observed. If libido falls to pre-administration levels, administration can be resumed.

In exemplary embodiments, the fenugreek seed extract is administered orally. Oral administration can be accomplished by incorporating the fenugreek seed extract into an oral dosage form such as a troche, tablet, sachet, suspension, solution, pill or capsule. Alternatively, the fenugreek seed extract can be orally administered by mixing with a food or a drink. Solid oral dosage forms, for example tablets and capsules, are particular examples of embodiments. In exemplary embodiments, the fenugreek seed extract is administered in the form of a capsule.

For purposes of formulation or administration, the fenugreek seed extract may be present in a composition that includes other inactive ingredients or excipients that are biologically acceptable, such as commonly used pharmaceutical excipients. Examples of inactive ingredients include maltodextrin and gelatin. A composition can be formulated to include the fenugreek seed extract and an acceptable carrier. An acceptable carrier is a material that is not biologically or otherwise undesirable, i.e., the material may be administered without causing any undesirable biological effects or interacting in a deleterious manner with any of the other components of the composition in which it is contained. The carrier would naturally be selected to minimize any degradation of the fenugreek extract components and to minimize any adverse side effects in the subject, as would be well known to one of skill in the art. For a discussion of acceptable carriers and other components of compositions, see, e.g., Remington's Pharmaceutical Sciences, 18th ed., Mack Publishing Company, 1990. One skilled in the art will appreciate that the particular composition will depend, in part, upon the chosen route of administration. Accordingly, there are a wide variety of suitable formulations of compositions of the present invention.

A tablet comprising the fenugreek extract may be made, for example, by compressing or molding the fenugreek extract, optionally containing one or more additional components. Compressed tablets may be prepared by compressing, in a suitable device, the fenugreek extract in a free-flowing form such as a powder or granular preparation, optionally mixed with one or more of a binder, a lubricant, a glidant, an excipient, a surface active agent, and a dispersing agent. Molded tablets may be made by molding, in a suitable device, a mixture of the fenugreek extract, an acceptable carrier, and at least sufficient liquid to moisten the mixture.

Tablets may be non-coated or they may be coated using methods known in the art or methods to be developed. Coated tablets may be formulated for delayed disintegration in the gastrointestinal tract of a subject, for example, by use of an enteric coating, thereby providing sustained release and absorption of the fenugreek extract. Tablets may further comprise a sweetening agent, a flavoring agent, a coloring agent, a preservative, or some combination of these in order to provide elegant and palatable preparation.

Hard capsules comprising the fenugreek extract may be made using a physiologically degradable composition, such as gelatin. Such hard capsules comprise the fenugreek extract, and may further comprise additional components including, for example, an inert solid diluent. Soft gelatin capsules comprising the fenugreek extract may be made using a physiologically degradable composition, such as gelatin. Such soft capsules comprise the fenugreek extract, which may be mixed with water or an oil medium.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

EXAMPLE 1

A randomized double blind study of the efficacy of fenugreek seed extract was conducted as follows:

Approximately 60-80 female subjects aged between 25-50 years of age were recruited and randomly allocated to either the placebo comparator group (n=40) or the active intervention group (n=40). The active intervention group was administered the fenugreek seed extract. The participants were supplied with laboratory pathology collection forms to complete blood tests before commencing with the study. The blood tests were not part of the screening process; however, the blood results were reviewed prior to participants commencing the product study and results must be in normal healthy reference range to continue.

Participants were assessed by conventionally used and validated questionnaires including the overall sexual response and the individual components of the sexual response: Sexual Cognition/Fantasy, Sexual Arousal, Sexual Behavior/Experience, Orgasm and Sexual Drive/Relationship using the DISF-SR QOL scores as primary endpoints. Improvement of sexual function and general quality of life was also assessed by evaluating the female hormone profiles before and after treatment.

Fenugreek seed extract or placebo was administered orally, approximately one hour before the morning meal and again one hour before the evening meal by capsules containing 300 mg LIBIFEM® fenugreek seed extract.

At two subsequent data collection points (weeks 4 and 8), the participants were assessed for any changes to lifestyle and health/medical status (via phone/clinic appointment) and completed Case Record Forms (CRFs). During week 7 (prior to completion of the trial), participants had blood collected for post-trial analysis. Within one week of completion of the trial, a face-to-face trial-exit interview was conducted with each trial subject to collect further data and assess the participant's health and wellbeing.

Participants were monitored for compliance with the protocol by a combination of telephone and email communications. Interim reporting of project status and adverse drug reactions was provided to the sponsor and Human Research Ethic Committee as requested.

Participants in the active intervention group were found to have enhanced libido in comparison to the placebo comparator group as indicated by at least one measure of libido.

EXAMPLE 2

Influence of Libifem, an extract of *Trigonella foenum-graecum* (Fenugreek), on sexual function, hormones and metabolism in healthy menstruating women, in a randomized placebo controlled study.

OBJECTIVES: The aim of the clinical trial was to evaluate the effect of Libifem (*Trigonella foenum-graecum* (Fenugreek) extract) on sexual function, hormonal profile and metabolism in healthy menstruating women in stable relationships.

DESIGN: This was a short-term, phase III, single site, double-blind, randomized, placebo-controlled study. The trial was conducted on 80 healthy menstruating women, with regular menstrual cycles, aged 21 to 49, in Brisbane in Australia. A detailed outline of this study is provided in FIG. 1.

Interventions: The participants were randomized to an oral dose of active treatment (300 mg Libifem) or placebo treatment twice per day over 2 menstrual cycles, starting in follicular phase of the menstrual cycle.

Outcome Measures: Sexual functioning was measured using the DISF-SR and FSFI self-administered questionnaires at baseline, 4 weeks and 8 weeks. The sex hormone profile (DHEA, progesterone, androstenedione, testosterone, oestradiol as well as LH, FSH and SHGB) was measured at baseline and 8 weeks. Specific markers of metabolism including the following tests: blood glucose, liver and renal function and total cholesterol levels, were also measured at baseline and at week 8. The influence of stress, fatigue and quality of the relationship with partner was measured using the PSS, MFSI and Dimensional Relationship Quality (DRQ) measures, respectively. The DRQ was used to assess the health of the relationship of the participant and their partner. It is a 32-item measure of relational intimacy. This DRQ subscale has been shown to be reliable and valid measures of relationship intimacy across multiple countries. The intimacy subscale includes items assessing empathy, openness, and trust in the relationship. Items consist of Likert responses coded so that higher scores indicate higher relational intimacy. Subscale scores are obtained by summing individual items.

RESULTS: Sexual functioning as measured by both the DISF-SR and the FSFI questionnaires showed a significant increase in those participants in the active treatment group after 8 weeks. There were significant increases in the sub-analysis of the 5 domains of the DISF-SR; sexual cognition, sexual arousal, sexual experience, orgasm and sexual drive/relationship at week 4 and week 8. Likewise, there was a significant change in the domains of the FSFI, namely arousal at week 8.

Overall, sexual functioning did not change in the placebo group. The placebo group showed no difference in the DISF-SR domain scores except for a significant increase in sexual drive/relationship at week 8 of treatment. Likewise, there was a no significant change in the domains of the FSFI. Analysis of the sex hormone levels after 8 weeks of treatment showed a significant increase in oestrodiol levels in the active group compared to the placebo group. There were no significant differences in any hormones in the placebo group. There was no difference in the other markers of metabolism after treatment in either group.

CONCLUSION: The results indicate that Libifem is an effective treatment to improve sexual function in otherwise healthy women and the biochemical mechanism may involve a restoration or maintenance of healthy oestradiol levels.

Materials and Methods

Figure 1:
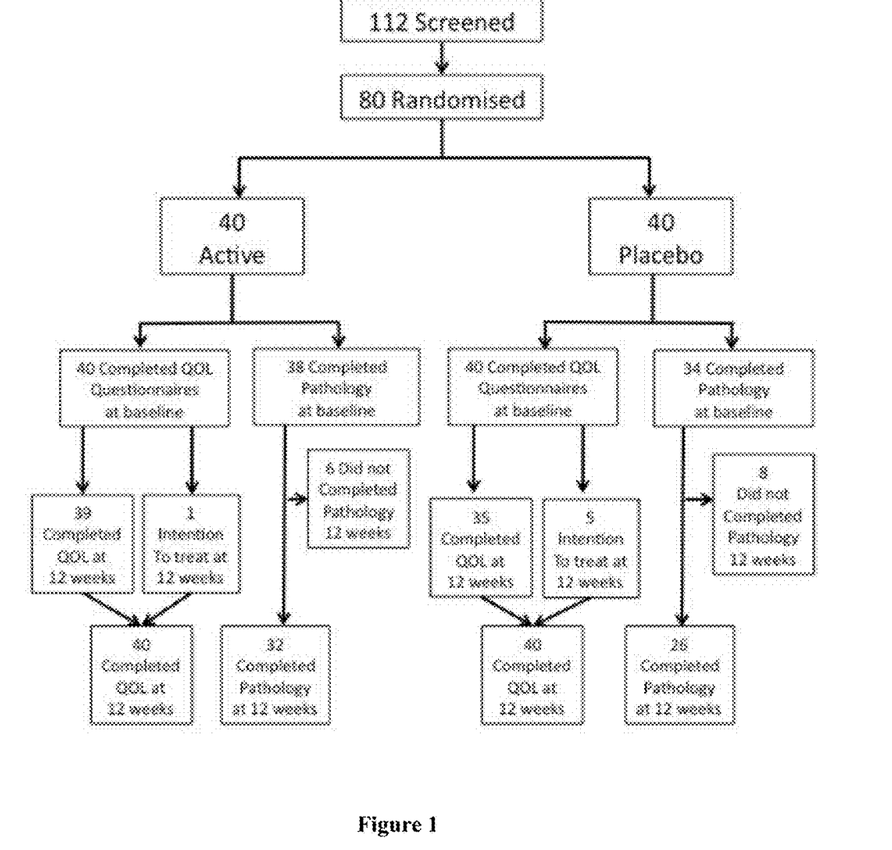
FIG. 1 is a flowchart of subject participation in trial.

Trial Design:

This study was a single site, parallel randomized double blind clinical trial of 80 healthy menstruating women, with 1:1 allocation ratio to either an active (n=40) or placebo (n=40) treatment (FIG. 1).

Participants:

Inclusion criteria: The participants were healthy menstruating women with regular menstrual cycles (between 28-34 days), aged between 21-50 years of age. Healthy was defined as being Body Mass Index (BMI) <35, blood pressure <130/90 and normal fasting blood glucose levels and with no diagnosed chronic diseases or prescribed pharmaceutical medications for a chronic disease. All participants were in a stable monogamous sexual relationship that was perceived to be secure and communicative, with a partner with normal sexual function. They believed that the low sexual desire was not caused by relationship/partner problems but that they had a low sex drive and were interested in increasing sexual function and libido. Sexual Dysfunction was assessed using the Female Sexual Function Index (FSFI). The FSFI was developed for the specific purpose of assessing the domains of sexual functioning (e.g. sexual desire, arousal, orgasm, satisfaction and pain) in clinical trials. It is not a measure of sexual experience, knowledge, attitudes, or interpersonal functioning in women. The clinical cut-off point for not having sexual dysfunction was defined as a score of >26 (Weigel et al 2005). All women were required to be on the contraceptive pill and/or were using other forms of contraception (including barrier method) to prevent pregnancy.

Exclusion criteria: The women were excluded from participating in the study if they had received androgen therapy at any time during the past 3 months, were pregnant or attempting to conceive, had been breastfeeding or be lactating for at least 3 months prior to study. They were also excluded if they had experienced any chronic or acute life stress relating to any major life change, were experiencing depression and/or receiving medication for such illness or disorder, were receiving statins or other drugs known to impact on steroid hormone levels, had a major illness, active gall bladder disease, or gynaecological or breast surgery within the last 6 months, had a history of breast, endometrial, or other gynaecological cancer at any time before study participation or other cancer within the last 5 years, were on medication for diabetes, had a history of cerebrovascular disease, thrombo-embolic disorders, heart attack, or angina at any time before study participation or thrombophlebitis within the last 5 years. In addition, women that were taking drugs that had anticoagulation and antiplatelet effects (such as aspirin, diclofenac (Voltaren, Clonac, Diclohexal, Dinac, Fenac), meloxicam (Mobic, Movelis), piroxicam (Mobilis, Feldene), ibuprofen (Brufen, Rafen, Neurofen), and naproxen (Proxen, Naprosyn, lnza, Crysanal, Naprogesic) on a daily basis for any conditions were excluded.

Recruitment and Enrollment:

Potential participants were recruited from databases and public media outlets in Brisbane, Australia. They were screened initially via on-line screening, followed by a telephone screening, prior to an initial baseline interview, at which each participant completed the consent form.

Trial Procedures and Compliance

At the baseline interview, a medical history, a medical assessment and the quality of life questionnaires (discussed below) were completed. Participants completed a blood test for Red Blood Cell count (RBC), E/LFT (electrolyte/liver function test) and hormone profile, in a fasting state on the morning of either day 7, 8 or 9, (during the follicular stage) of their next menstrual cycle. Participants were also given the investigational product with instructions to commence the treatment once the initial blood test had been done. At month 1, the participants completed the libido questionnaire (DISF-SR) only. At month 2 (on day 7, 8 or 9), participants repeated the blood tests. Within one week of completion of the trial, a trial-exit interview was conducted and all of the quality of life questionnaires completed again. Participants were monitored for compliance with the protocol by a combination of telephone and email communications and the return of bottles and unused product at completion of the trial.

Interventions:

The investigational product contained 300 mg of Libifem, a *Trigonella foenum graecum* (Fenugreek) seed extract (dry concentrate 33:1, equivalent to 9.9 g dry herb) and 30 mg of the flow agent maltadextrin, in a 2-piece white hard gelatin non-marked capsule size 0. The placebo product contains 330 mg maltodextrin only, also in a size 2 non-marked, hard gelatin capsule. Libifem and placebo capsules were administered as 2 capsules per day with food, 1 before breakfast and 1 before dinner, for the 2 months of the study.

Primary Outcomes
Changes in Sexual Function

Sexual function was assessed at baseline, month 1 and month 2 using the total scores and the domain scores of the validated quantitative Derogatis Interview for Sexual Functioning (DISF-SR) (Female). The DISF-SR (female) is a brief semi structured interview designed to provide the quality of an individual's current sexual functioning in quantitative terms. The DISF represents quality of current sexual functioning in a multidomain format, which parallels the phases of the sexual response cycle (Masters & Johnson, 1966). The 25 interview items of the DISF are arranged into five domains of sexual functioning: I. Sexual Cognition/Fantasy, II. Sexual Arousal III. Sexual Behaviour/Experience, IV. Orgasm, V. Sexual Drive/Relationship.

Sexual Function was also assessed at baseline and month 2 using the Female Sexual Function Index (FSFI). The FSFI is a 19 item questionnaire divided into 6 content domains; desire, arousal, lubrication, orgasm, satisfaction and pain. (Rosen, 2000; Meston, 2003) It is not a measure of sexual experience, knowledge, attitudes, or interpersonal functioning in women. The differentiation point for sexual dysfunction was defined as a score of <26 (Weigel et al., 2005).

Secondary Outcomes:
1. Influence on Sex Hormone Levels

The following hormones were measured at baseline and month 2: total testosterone, free testosterone, sex hormone binding globulin (SHBG), oestradiol (E2), androstenedione, dehydroepiandrosterone (DHEA), follicle stimulating hormone (FSH), luteinizing hormone (LH), progesterone, and prolactin. Blood was collected from participants in a fasting state, after rising during follicular phase of the menstrual cycle. Blood collection was carried out at QML Pathology (QML) in Brisbane. QML was responsible for collection, transport, analysis, and reporting of findings in accordance with applicable guidelines.

Influence on Body Weight, BMI and Metabolic Parameters

The following metabolic parameters were measured at baseline and month 2: full blood count (FBC), (E/LFT), plasma proteins albumin and globulin, cholesterol, triglycerides and blood glucose.

3. Relationships and Correlations with Stress, Fatigue and Relationship Quality:

The Perceived Stress Scale (PSS) was used to assess stress at baseline and at month 2. The PSS is the most widely used psychological instrument for measuring the perception of stress. It is a measure of the degree to which situations in one's life are appraised as stressful. Items were designed to tap how unpredictable, uncontrollable, and overloaded respondents find their lives. The scale also includes a number of direct queries about current levels of experienced stress. The Multi-dimensional Fatigue Symptom Inventory (MFSI) was used to assess stress at baseline and at month 2. The MFSI provides a total score for fatigue and also included are individual domains of general, emotional, physical, mental health and vigour as separate aspects to fatigue. The DRQ was used to assess the health of the relationship of the participant and their partner. It is a 32-item measure of relational intimacy. This DRQ subscale has been shown to be reliable and valid measures of relationship intimacy across multiple countries.

4. Safety:

Safety and tolerability were determined by electrolyte/liver function test (E/LFT), full blood count (FBC), sex hormone levels, blood glucose and cholesterol levels and participant reporting of their menstrual cycle pattern and any adverse events.

Randomization:

The randomization of participants to active treatment or placebo was conducted independently to the investigators, using the Random Allocation Software. The randomization code was a sequential number generated by simple randomization of numbers 1-80 into 2 arms of equal numbers (n=40) and product provided to investigators in 80 identical sequentially numbered bottles. The participants were allocated a numbered bottle by the clinical staff upon enrolment (baseline interview) into the study, with both the clinical staff and the participants being blinded to product allocation.

Sample Size and Statistical Analysis:

Sample size: A minimum number of 60 participants per group were required to achieve a statistically power of 80% on the basis of a 20% increase in average sexual function as measured by the total domain score of the DISF-SR (female). The primary endpoint, DISF-SR total score, the individual domain scores and the other QOL data were analyzed for significance using Wilcoxin Signed rank test. The pathology results and FSFI data was analyzed for significance using T-Tests. The correlations were analyzed using the Pearson Correlation Co-efficient.

Ethical Approval and Clinical Trial Registration:

The study was carried out according to the principles expressed in the Declaration of Helsinki and was approved by the Queensland Clinical Trial Network Human Research Ethics Committee (QCTN) No: 2011001. The clinical trial was registered with the Australia/New Zealand Clinical Trial Registry (ANZCTR) No: 12611001031954

Results

1. Participant Demographics:

The demographics of the study group are summarized in Table 1 below. The active and placebo groups were well matched for age, active group 34.9±7.6 years, placebo group, 34.6±8.0. Likewise, the average BMI for both groups was also similar, (active group 24.8±5.0; placebo group 24.7±6.0) and considered in the normal healthy weight range. With regards to lifestyle, most women in both groups (active group at 90%; placebo group at 95%) were non-smokers. The majority of both groups (65% active, 80% placebo) classified themselves as social drinkers. In both groups, the majority of participants reported undertaking regular exercise (82.5%). The active group included women who had up to 4 children (average of 1.1) compared with the placebo group which included women with up to only 3 children (average of 0.9).

TABLE 1

Participant Demographics

| | Total (n = 80) | Placebo (n = 40) | Active (n = 40) |
|---|---|---|---|
| Age | | | |
| Average (SD) | 34.9 (7.9) | 34.6 (8.0) | 34.9 (7.6) |
| Range | 20-49 | 22-49 | 20-49 |
| Height (m) (SD) | 1.67 (6.6) | 1.67 (6.3) | 1.67 (6.7) |
| Weight (kg) (SD) | 69.4 (16.1) | 68.7 (16.8) | 69.5 (15.0) |
| Body Mass Index (BMI) (SD) | 24.9 (5.5) | 24.7 (6.0) | 24.8 (5.0) |
| Number of children | | | |
| Average | 1.1 | 0.9 | 1.1 |
| Range | 0-4 | 0-3 | 0-4 |
| Smoking | | | |
| No (Number, %) | 74/80 (92.5%) | 38/40 (95%) | 36/40 (90%) |
| Yes (Number, %) | 6/80 (7.5%) | 2/40 (5%) | 4/40 (10%) |
| Alcohol intake | | | |
| No (Number, %) | 22/80 (27.5%) | 8/40 (20%) | 14/40 (35%) |
| Social (Number, %) | 58/80 (72.5%) | 32/40 (80%) | 26/40 (65%) |
| Exercise Patterns | | | |
| None (Number, %) | 14/80 (17.5%) | 7/40 (17.5%) | 7/40 (17.5%) |
| Regular (Number, %) | 66/80 (82.5%) | 33/40 (82.5%) | 33/40 (82.5%) |
| Oral Contraceptive Pill (OCP) | | | |
| Yes (Number, %) | 26/80 (32.5%) | 15 (37.5%) | 11 (27.5%) |
| No (Number, %) | 54/80 (67.5%) | 25 (62.5%) | 29 (72.5%) |

In this study group, 71 women completed the pathology tests at baseline: active (n=38) and placebo (n=34). All women were considered healthy by definition of having normal RBC studies (red cell count (RCC), haematocrit, mean corpuscular volume (MCV), mean corpuscular hemoglobin (MCH)), normal fasting cholesterol and triglyceride levels, normal fasting blood sugar levels, normal liver and kidney function.

Sexual health: All women had regular menstrual cycles ranging from 28-34 days. All women were using a form of contraception, either Oral Contraception Pill (OCP) (Active (11/40); placebo (15/40)) or barrier methods (Active (29/40); placebo (25/40). The menstrual pain scores were similar in both groups. However, those women on the OCP suffered less menstrual pain than those women using barrier methods to prevent pregnancy. The menstrual cycle hormones (LH, FSH, progesterone and oestrogen) were within range for all participants and were indicative of being in the follicular phase of the menstrual cycle for healthy menstruating women. There was no statistical difference between the levels of sex hormones DHEA, androstenedione, testosterone, oestradiol, progesterone, prolactin, and SGBP, which were within healthy reference range for both groups. Sexual dysfunction on the FSFI: there was no significant difference in sexual functioning between the 2 groups at baseline. Sexual functioning was measured by the DISF-SR questionnaire. There was no significant difference between the sexual functioning scores for the active group or the placebo group at baseline (57.8 and 65.9 respectively).

Quality of Life: Relationship quality; the quality of the participants relationship with their partner was assessed using the DAS scale. The women scored relatively high on this scale (active 104.4 and placebo 102.2) indicating that they were in a secure relationship, and content at least with aspects of the relationship other than sexual functioning. Stress and fatigue: The baseline results showed that there was no significant difference between the active group and the placebo for stress. The fatigue scores as measured by the MFSI were also comparable between active and placebo groups.

2. Baseline Correlations

Libido was negatively correlated with age, but was not correlated with any other health or hormone parameters. Age was positively correlated with weight/Body Mass Index (BMI) and number of children.

3. Effect of Libifem in Female Sexual Functioning

Figure 2:
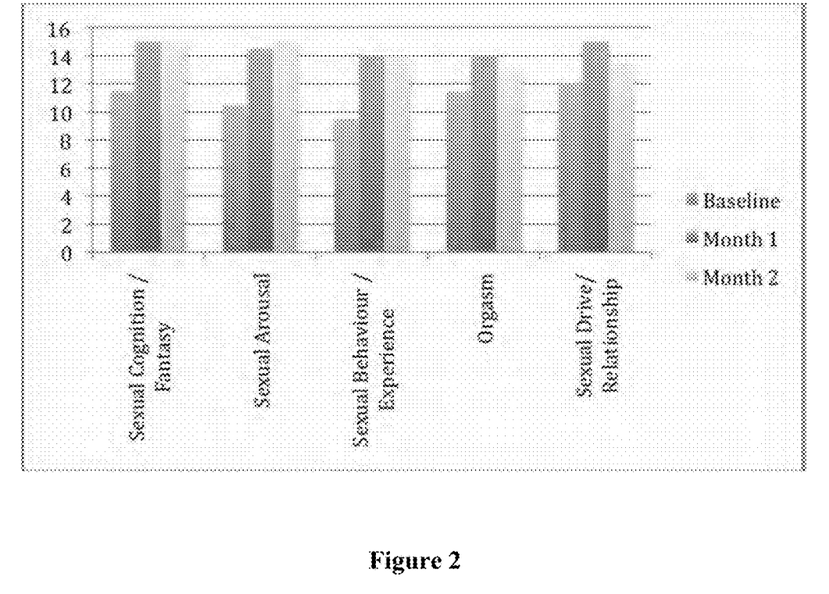
FIG. 2 shows DISF domain scores for Active group at Baseline, month 1 and month 2.
Figure 3:
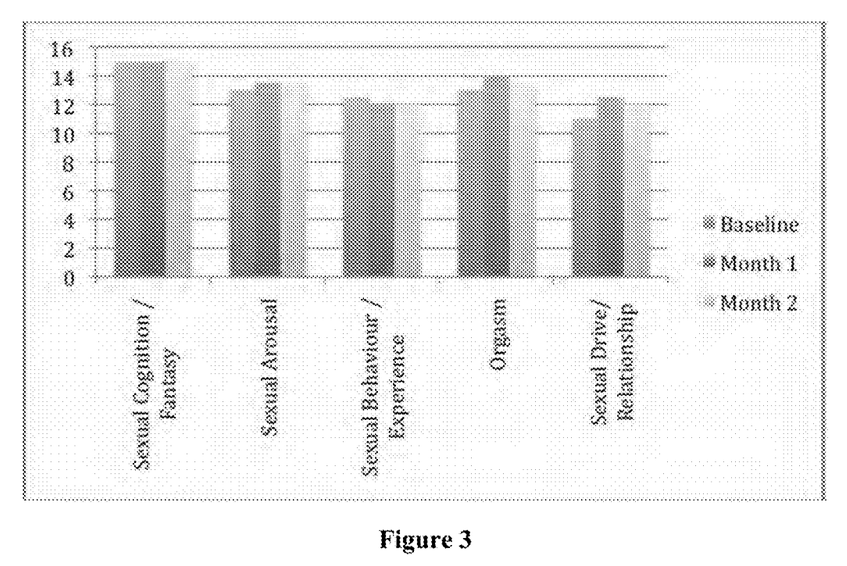
FIG. 3 shows DISF domain scores for Placebo group at Baseline, month 1 and month 2.

Sexual function using the DISF-SR was measured at baseline prior to treatment, month 1 (mid-point) and at month 2. (FIGS. 2, 3).

Total Score:

The total DISF-SR score median for the active group (n=40) at baseline was 53.0 (40.25, 73.75). The total score after month 1 was 73.0, (47.0, 92.0), a significant increase over baseline, and it remained significant at month 2 at 76.0 (44.0, 98.4). The total DISF-SR for the placebo group (n=40) at baseline was 66.5 (51.5, 77.75) and this increased to 67.0 (53.5, 81.34) at month 1 and to 68.5 (48.5, 80.75) at month 2, but this increase was not statistically significant.

Domain 1—Sexual Cognition/Fantasy

In the active group, the domain score for sexual cognition/fantasy increased significantly from 11.5 (7.0, 18.75) at baseline to 15.0 (10.25, 20.75) at month 1 and remained stable at 15.0 at month 2 (9.25, 24.75). The placebo group recorded a baseline value of 15 (8.5, 20.75) but this remained unchanged over the study period; month 1 value of 15 (10.0, 23.75), month 2 value of 15 (7.5, 20.75).

Domain 2—Sexual Arousal

In the Active group, the domain score increased significantly from 10.5 (7.0, 14.0) at baseline to 14.5 (9.25, 19.0)

at month 1 and increased slightly to 15.0 (9.25, 20.0). The placebo group recorded a baseline value of 13.0 (9.2, 16.75) but this increased slightly to 13.5 (9.0, 17.38) at month and remained constant at month 2 (9.25, 17.38).

Domain 3—Sexual Experience

In the Active group, the domain score increased significantly from 9.5 (7.0, 14.0) at baseline to 14.0 (10.25, 19.0) at month 1 and remained at 14.0 (8.25, 19.0) at month 2. The placebo group recorded a baseline value of 12.5 (8.2, 15.0) and this reduced to 12.0 (9.0, 16.0) and remained at 12 (7.25, 16.75) at month 2. The frequency of sexual activity was assessed using DISF Q 3.5 "During the past 30 days, or since the last time you filled out this inventory, how often did you engage in sexual intercourse, oral sex, etc." The frequency in active group increased from 1-2 times per month to average of once per week. The frequency of sexual activity in the placebo group remained the same at month 2, at 1-2 times per month.

Domain 4—Orgasm

In the Active group, the domain score increased significantly from 11.5 (7.0, 14.75) at baseline to 14.0 (7.0, 18.0) at month 1 and slightly decreased to 13.0 (7.0, 19.0) at month 2. The placebo group recorded a baseline value of 13.0 (11.0, 16.0) and this increased to 14.0 (11.25, 18.0) and then reduced to 13.5 (12.0, 17.75) at month 2.

Domain 5 Sexual Drive/Relationship

In the Active group, the domain score increased significantly from 12.0 (8.25, 14.5) at baseline to 15.0 (10.0, 18.0) at month 1 and slightly decreased to 13.5 (10.0, 17.75) at month 2. The placebo group recorded a baseline value of 11.0 (9.25, 14.75) and this increased to 12.5 (10.0, 15.0) and then reduced to 12.0 (10.0, 16.0) at month 2.

FSFI

Figure 4A:
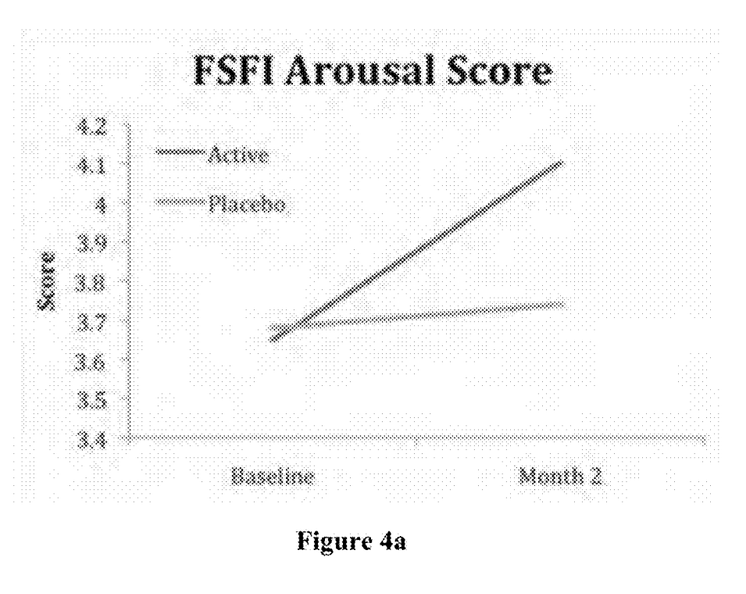
FIG. 4a shows the FSFI arousal domain score.
Figure 4B:
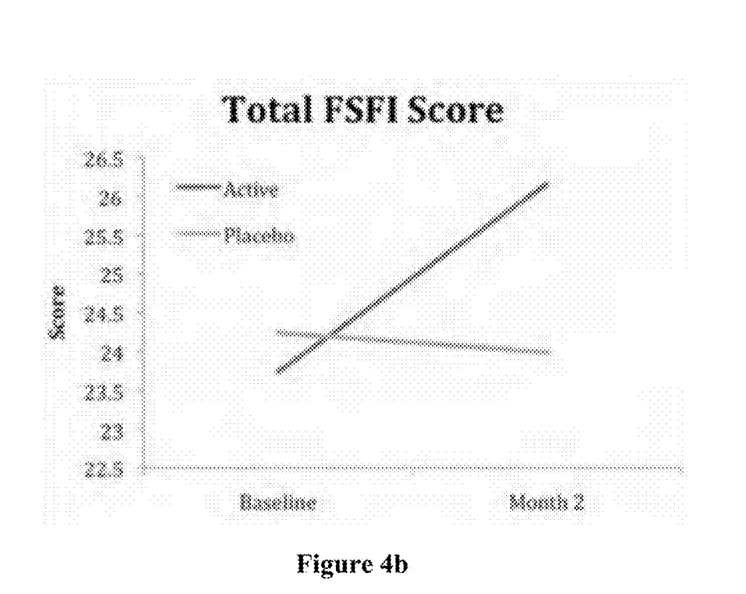
FIG. 4b shows the total FSFI score.

Sexual function using the FSFI was measured at baseline prior to treatment and at month 2. There was a significant difference between the active treatment group and the placebo group at month 2 in the domains of Total score and Arousal at month 2. (See FIG. 4 a,b).

4. Effect of Libifem on Metabolism and Sex Hormones

The effect on general metabolism from Libifem administration at 300 mg twice/day for 2 months was also measured. The average body weights did not change for either group over the study period, active treatment group (69.5 kg and 69.4 kg respectively), placebo group (68.7 kg at baseline and 8 weeks). There were no changes in red blood cell parameters, liver function tests and triglyceride levels in either active treatment or placebo groups before or after treatment at 8 weeks.

Figure 5:
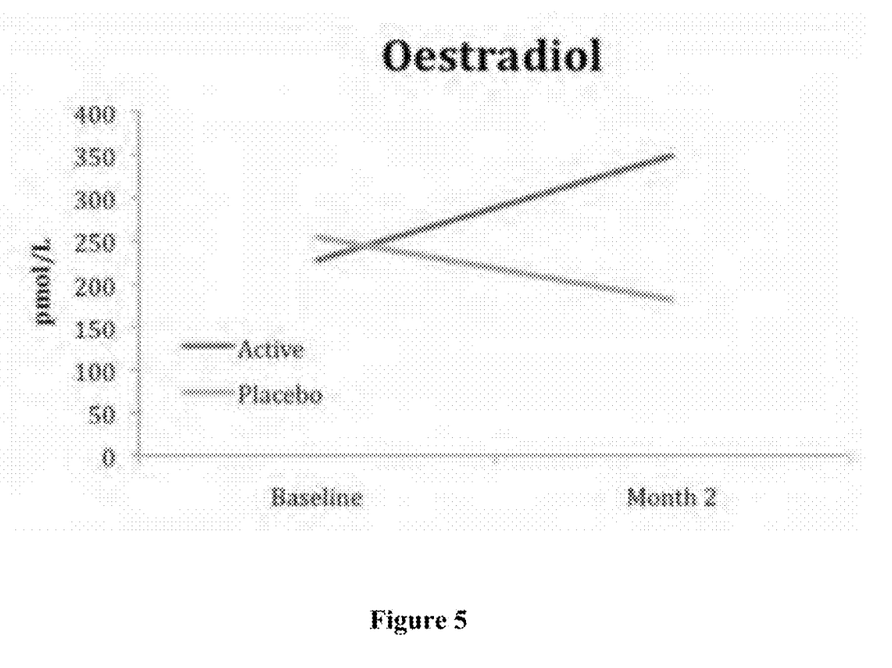
FIG. 5 shows the levels of Oestradiol at baseline and month 1 for active treatment group and placebo group.
Figure 6A:
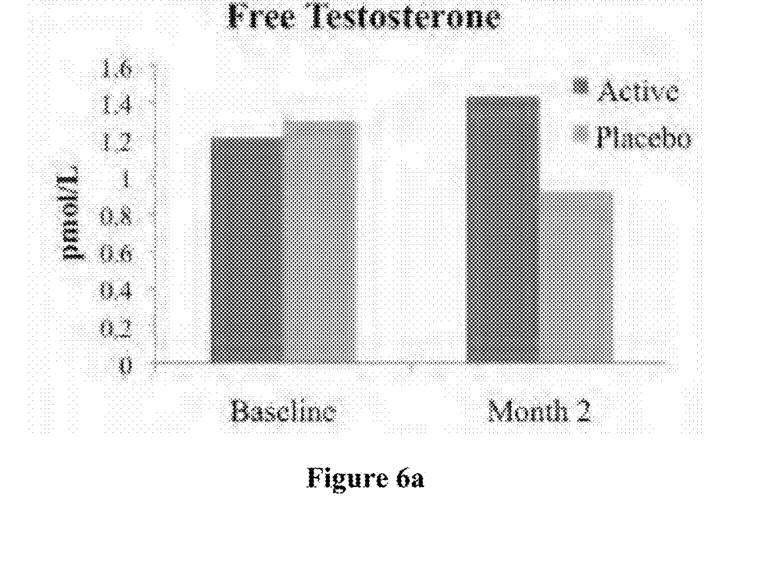
FIG. 6a shows the average free testosterone.
Figure 6B:
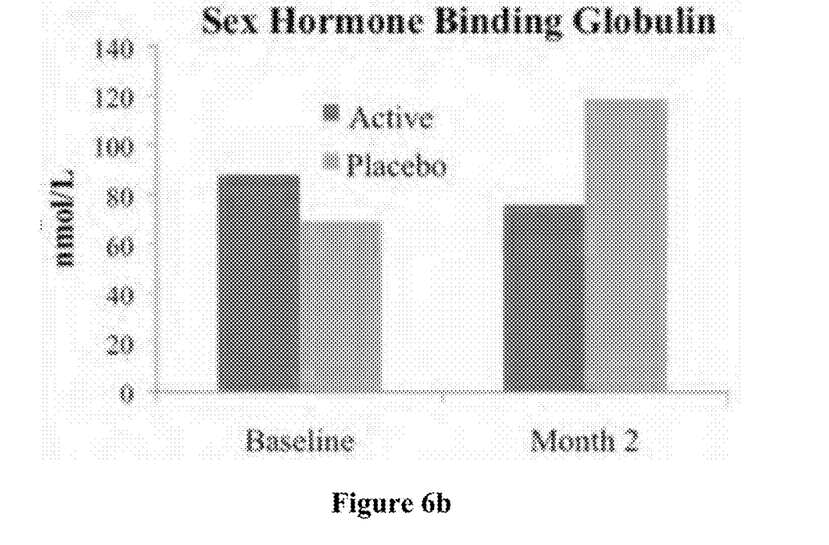
FIG. 6b shows sex hormone binding globulin levels.

The analysis of hormone changes between baseline and month 2 were conducted on the participants who completed both baseline and month 2 pathology tests (active n=32 and placebo n=26). The hormones forming the chain of steroid synthesis, in order, cholesterol, DHEA, and androstenedione were similar at baseline and at month 2. There was no significant intergroup difference between active treatment group and placebo groups at month 2. Grouped together, the sex hormones (LH, FSH, ES) in the placebo group were in the higher levels (still within the reference range but not significantly different) in comparison to the active treatment group at baseline. There was no significant difference between the baseline and month 2 results for either group for LH or FSH levels. However, oestradiol, increased from 202.9-327.2 pmol/L in the active group and there was a significant intergroup difference between active treatment group and placebo group at month 2 (p<0.05). (see FIG. 5). The levels of free testosterone increased and SHBG decreased in the active treatment group and the opposite effect was observed in the placebo group (FIG. 6).

5. Effect of Libifem on Quality of Life

There was no difference in the Relationship quality between active treatment group and placebo group at baseline and month 2. Both groups did score highly at baseline, establishing that the women were in a stable and secure relationship, despite the low sexual functioning. However, in both groups a further increase in relationship quality at month 2 was observed.

6. Adverse Reactions

There were no major adverse reactions reported as a result of Libifem use over the 2 months. However, there were reports of exacerbation of migraines (in 2 women in the active group) within 1 month of treatment. There were also 2 reports of gastrointestinal upset, namely indigestion/reflux in 2 participants in the active group.

CONCLUSIONS

There are a number of implications that can be gained from this study. It has provided further information, to the growing body of evidence, that *Trigonella foenum-graecum* seed extract is a safe and effective botanical medicine for use in hormonal balance, including the support of sexual function in healthy women. It provides further evidence that its mechanism of action is due to regulation of oestradiol balance in women. In summary, Libifem is safe and effective treatment for supporting sexual functioning in healthy menstruating women, including those on the OCP, without altering the duration of the menstrual cycle. The mechanism by which is exerts its effect is likely to include the influencing of the testosterone/oestradiol ratio.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

We claim:

1. A method of enhancing female libido comprising administering an effective amount of from about 300 to about 1000 mg per day of a fenugreek seed extract to a female mammal in need thereof and thereby modifying a behavioral characteristic indicative of an increase in female libido or modifying a biological response indicative of an increase in female libido; wherein the fenugreek seed extract is a hydro alcoholic extract and is dried to form a dry concentrate of at least 33:1 of the fenugreek seed.

2. The method of claim 1, wherein the behavioral characteristic indicative of an increase in female libido is selected from the group consisting of increasing sexual fantasy, increasing arousal, increasing sex drive, enhancing partner relationship and increasing desire for sexual activity.

3. The method of claim 1, wherein the biological response indicative of an increase in female libido is selected from the group consisting of increasing an ability to achieve orgasm, decreasing dyspareunia, and increasing vaginal lubrication or dilation.

4. The method of claim 1, wherein the biological response indicative of an increase in female libido is a change in the level of a sex steroid or hormone.

5. The method of claim 4, wherein the sex steroid or hormone is selected from the group consisting of total testosterone, free testosterone, sex hormone binding globulin, total estradiol free estradiol (E2), androstenedione, Dehydroepiandrosterone (DHEA), Dehydroepiandrosterone sulfate (DHEAS), Follicle Stimulating Hormone (FSH), and Luteinizing Hormone (LH).

6. The method of claim 1, wherein the effective amount is administered in two equal doses.

7. The method of claim 1, wherein the effective amount of fenugreek seed extract is about 600 mg per day.

8. The method of claim 7, wherein the effective amount is administered in two equal doses.

9. The method of claim 8, wherein the fenugreek seed extract is administered approximately one hour before a meal.

10. The method of claim 1, wherein the effective amount of fenugreek seed extract is 600 mg per day.

11. The method of claim 10, wherein the effective amount is administered in two equal doses.

12. The method of claim 11, wherein one dose of the fenugreek seed extract is administered approximately one hour before a morning meal and a second dose is administered approximately one hour before an evening meal.

13. The method of claim 1, wherein the female is a human.

14. The method of claim 1, wherein the fenugreek seed extract is administered in an oral dosage form.

15. The method of claim 1, wherein enhancing libido is evidenced by a statistically significant increase in one or more DISF domain scores.

16. The method of claim 1, wherein enhancing libido is evidenced by a statistically significant increase in one or more FSFI domain scores or in total FSFI score.

* * * * *

UNITED STATES PATENT AND TRADEMARK OFFICE
CERTIFICATE OF CORRECTION

PATENT NO. : 10,149,878 B2
APPLICATION NO. : 14/097465
DATED : December 11, 2018
INVENTOR(S) : Sunil Bhaskaran et al.

Page 1 of 1

It is certified that error appears in the above-identified patent and that said Letters Patent is hereby corrected as shown below:

On the Title Page

In the Inventor item (72), replace Ramasamy V. Venkatesh, Haikou (CN); Jith Veeravalli, Anaheim, CA (US) with -- Ramasamy V. Venkatesh, Hong Kong (CN); Jith Veeravalli, Irvine, CA (US) --

Signed and Sealed this
Sixteenth Day of July, 2019

Andrei Iancu
*Director of the United States Patent and Trademark Office*